(12) United States Patent
Mikami et al.

(10) Patent No.: US 7,289,232 B2
(45) Date of Patent: Oct. 30, 2007

(54) DIMENSION MEASUREMENT METHOD, METHOD OF MANUFACTURING SEMICONDUCTOR DEVICE, DIMENSION MEASUREMENT APPARATUS AND MEASUREMENT MARK

(75) Inventors: Toru Mikami, Kanagawa (JP); Toru Koike, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 376 days.

(21) Appl. No.: 10/980,285

(22) Filed: Nov. 4, 2004

(65) Prior Publication Data

US 2005/0151980 A1    Jul. 14, 2005

(30) Foreign Application Priority Data

Nov. 4, 2003 (JP) .............................. 2003-374849

(51) Int. Cl.
*G01B 11/00* (2006.01)
(52) U.S. Cl. ....................... 356/626; 356/401
(58) Field of Classification Search ................ 356/626, 356/636, 401, 625, 635
See application file for complete search history.

(56) References Cited

U.S. PATENT DOCUMENTS

| | | | | |
|---|---|---|---|---|
| 4,236,823 A | * | 12/1980 | Roach et al. ................ | 356/521 |
| 4,746,792 A | * | 5/1988 | Dil ............................... | 356/499 |
| 5,165,045 A | * | 11/1992 | Eselun .................... | 250/237 G |
| 5,900,633 A | * | 5/1999 | Solomon et al. ........ | 250/339.08 |
| 5,963,329 A | * | 10/1999 | Conrad et al. ............. | 356/613 |
| 6,483,580 B1 | * | 11/2002 | Xu et al. ..................... | 356/300 |
| 6,590,656 B2 | * | 7/2003 | Xu et al. ..................... | 356/369 |
| 6,608,690 B2 | | 8/2003 | Niu et al. | |
| 6,609,086 B1 | * | 8/2003 | Bao et al. .................... | 702/189 |
| 6,721,052 B2 | * | 4/2004 | Zhao et al. .................. | 356/369 |
| 6,771,374 B1 | * | 8/2004 | Rangarajan et al. ........ | 356/445 |
| 6,775,015 B2 | * | 8/2004 | Bischoff et al. ............ | 356/636 |
| 6,825,924 B2 | * | 11/2004 | Uda et al. ................. | 356/237.5 |
| 6,850,333 B1 | * | 2/2005 | Johnson et al. ............. | 356/625 |
| 6,867,862 B2 | * | 3/2005 | Nikoonahad ................ | 356/340 |
| 6,952,271 B2 | * | 10/2005 | Niu et al. .................... | 356/625 |
| 7,142,282 B2 | * | 11/2006 | Borodovsky ................. | 355/53 |

OTHER PUBLICATIONS

Stelzer, Ernst H. K., "Light Microscopy: Beyond the diffraction limit?", Nature 417, 806-807, Jun. 20, 2002.*

* cited by examiner

*Primary Examiner*—Gregory J. Toatley, Jr.
*Assistant Examiner*—Scott M Richey
(74) *Attorney, Agent, or Firm*—Finnegan, Henderson, Farabow, Garrett & Dunner, L.L.P.

(57) ABSTRACT

A dimension measurement method includes irradiating a measurement mark on a sample on which a pattern to be measured is formed with light from a measurement direction, detecting reflected diffracted light from the measurement mark to measure intensity thereof, and calculating a shape parameter of the pattern on the basis of the measured intensity, the measurement mark having measurement patterns which have the same shape as at least part of the pattern and are arranged in rows and columns, the columns being composed of the measurement patterns disposed with a predeter period in the direction perpendicular to the measurement direction, wherein a relation between a wavelength of the light and the period is adjusted so that the measurement mark generates the reflected diffracted light substantially the same as reflected diffracted light which would be generated when the column is assumed to be a continuous line pattern.

14 Claims, 15 Drawing Sheets

DIMENSION MEASUREMENT METHOD, METHOD OF MANUFACTURING SEMICONDUCTOR DEVICE, DIMENSION MEASUREMENT APPARATUS AND MEASUREMENT MARK

CROSS REFERENCE TO RELATED APPLICATION

This application claims benefit of priority under 35USC §119 to Japanese Patent Application No. 2003-374849, filed on Nov. 4, 2003, the contents of which are incorporated by reference herein.

BACKGROUND OF THE INVENTION

1. Field of the Invention

The present invention relates to a dimension measurement method, a method of manufacturing a semiconductor device, a dimension measurement apparatus and a measurement mark, and is directed, for example, to scatterometry of a shape parameter of patterns formed in a manufacturing process of a semiconductor device.

2. Description of the Related Art

A technique to measure dimensions of a pattern in a manufacturing process of a semiconductor device has heretofore been limited substantially to a technique using a measurement mark in which a one-dimensional line-and-space pattern is formed, and has not been applicable to patterns having an arbitrary shape such as a hole pattern.

A related conventional art will be described referring to FIG. 13A to FIG. 17. FIGS. 13A and 13B show one example of the line-and-space measurement mark, wherein FIG. 13A is a plan view thereof and FIG. 13B is a sectional view along the cutting-plane line L-L of FIG. 13A. For a measurement mark MK100 shown in FIGS. 13A and 13B, a thin film is formed on an upper surface of a semiconductor wafer W, and trenches TG1 to TG4 are formed through processes using photolithography, etching and the like, thus forming one-dimensional line-and-space patterns in a plan view. In the measurement mark MK100, the trenches TG1 to TG4 are provided with widths LX1 to LX4 and depths DX1 to DX4, respectively.

FIG. 14 is a block diagram showing one example of a conventional dimension measurement apparatus according to the related conventional art. A dimension measurement apparatus 100 shown therein comprises a light source 110, a polarizer 112, a stage 140, an analyzer 114, an array of detectors 116, a computer 118 and a memory MR100. The light source 110 emits white light. The stage 140 moves the wafer W through revolving movement (in a RV direction) and translational movement (in a TR direction). The detectors 116 include a spectroscope. The memory MR100 has a plurality of storage areas, and stores measurement profile charts which will be described later, and also stores several values which will be candidates for an average value LXave of the widths LX1 to LX4 of the trenches TG1 to TG4 and several values which will be candidates for an average value DXave of the depths DX1 to DX4 of the trenches TG1 to TG4.

One example of a conventional dimension measurement method using the dimension measurement apparatus 100 shown in FIG. 14 will be described.

First, the stage 140 moves the wafer W in combination of the revolving movement in the RV direction and the translational movement in the TR direction such that the white light falls on the target measurement mark MK100. In the example shown in FIG. 14, the wafer W is moved so that its notch NT is directed downward of the drawing.

Next, the white light is emitted by the light source 110, turned into incident light Li via the polarizer 112, and then caused to obliquely fall on the measurement mark MK100 at an incidence angle θ. As reflected diffracted light Lr is generated from the measurement mark MK100, this reflected diffracted light Lr is detected by the detectors 116 via the analyzer 114, and a detection signal is sent to the computer 118. The computer 118 processes this detection signal and plots a measurement profile in a graph whose horizontal axis indicates a wavelength λ and whose vertical axis indicates reflected light intensity I as indicated by a broken line ML100 in FIG. 15, which is stored by the memory MR100. The computer 118 also derives, from the memory MR100, candidate values for the average value LXave of the widths and candidate values for the average value DXave of the depths of the line-and-space trench patterns, in order to substitute these values for a predetermined theoretical model such as RCWA. The computer 118 then, as represented by a full line TL100 in FIG. 15, plots theoretical profiles in the graph whose horizontal axis indicates the wavelength λ and whose vertical axis indicates reflected light intensity I, and identifies a theoretical profile which is the most approximate to the measurement profile ML100 among the plotted theoretical profiles, and then outputs, as measurement values, the candidate value for the average value LXave of the widths and the candidate value for the average value DXave of the depths that have been input when the identified theoretical profile is calculated.

In this way, according to the conventional method, the line-and-space patterns constituting the measurement mark MK100 are used, so that diffracted light due to periodic characteristics of the one-dimensional pattern alone is generated from these patterns, and the pattern dimension can be rapidly calculated by the conventional theoretical model such as RCWA.

However, the above-mentioned conventional method has not been applicable when patterns other than the line-and-space patterns are used for the measurement mark.

For example, in cylindrical hole patterns constituting a measurement mark MK120 shown in FIGS. 16A to 16C, the values of widths and depths may differ depending on the direction of measurement, and this is because the diffracted light is generated in both an X direction and a Y direction, that is, due to two-dimensional periodic characteristics: for example, widths LHX1 to LHX8 and depths DHX1 to DHX8 in the X direction, and for example, widths LHY1 to LHY8 and depths DHY1 to DHY8 in the Y direction. Therefore, even if the candidate values for an average value LHXave of the widths in the X direction, an average value DHXave of the depths in the X direction, an average value LHYave of the widths in the Y direction and an average value DHYave of the depths in the Y direction are input into the conventional theoretical model such as the RCWA method, a candidate profile for a theoretical model TL can not be calculated rapidly.

More specifically, a two-dimensional theoretical model has to be used to enhance measurement accuracy, and in that case measurement steps, the number of which corresponds to the square of the number of steps for a one-dimensional theoretical model, are needed for the calculation thereof, which is unpractical. Moreover, if the theoretical profile is calculated within a limited amount of time, a result will be far away from the measurement profile ML120 like a theoretical profile TL120 shown in FIG. 17, leading to a problem of significantly degraded measurement accuracy.

SUMMARY OF THE INVENTION

According to a first aspect of the invention, there is provided a dimension measurement method comprising:

irradiating a measurement mark with light, the measurement mark being formed on a sample on which a pattern to be measured is formed, the measurement mark comprising measurement patterns of the same shape as at least part of the pattern to be measured, the measurement patterns being arranged in a matrix constituted of measurement pattern columns which are repetitively disposed with a predetermined space in the direction of an arbitrary measurement direction which would provide a measurement target dimension of the pattern to be measured, said measurement pattern column being composed of the measurement patterns disposed with a predetermined period in the direction perpendicular to the measurement direction, and the light being fallen from the measurement direction;

detecting reflected diffracted light from the measurement mark to measure intensity thereof;

calculating a theoretical value of the intensity of the reflected diffracted light from a plurality of candidate values for the measurement target dimension; and outputting, as a measurement value of the measurement target dimension, the candidate value which provides a theoretical value most approximate to the measured intensity of the reflected diffracted light among the plurality of candidate values, wherein a relation between a wavelength of the light incident on the measurement mark and said period is adjusted so that the measurement mark generates the reflected diffracted light which is substantially the same as reflected diffracted light which would be generated when said pattern column is assumed to be a continuous line pattern.

According to a second aspect of the invention, there is provided a method of manufacturing a semiconductor device, comprising a dimension measurement method including:

irradiating a measurement mark with light, the measurement mark being formed on a sample on which a pattern to be measured is formed, the measurement mark comprising measurement patterns of the same shape as at least part of the pattern to be measured, the measurement patterns being arranged in a matrix constituted of measurement pattern columns which are repetitively disposed with a predetermined space in the direction of an arbitrary measurement direction which would provide a measurement target dimension of the pattern to be measured, said measurement pattern column being composed of the measurement patterns disposed with a predetermined period in the direction perpendicular to the measurement direction, and the light being fallen from the measurement direction;

detecting reflected diffracted light from the measurement mark to measure intensity thereof;

calculating a theoretical value of the intensity of the reflected diffracted light from a plurality of candidate values for the measurement target dimension; and outputting, as a measurement value of the measurement target dimension, the candidate value which provides a theoretical value most approximate to the measured intensity of the reflected diffracted light among the plurality of candidate values, wherein a relation between a wavelength of the light incident on the measurement mark and said period is adjusted so that the measurement mark generates the reflected diffracted light which is substantially the same as reflected diffracted light which would be generated when said pattern column is assumed to be a continuous line pattern.

According to a third aspect of the invention, there is provided a dimension measurement apparatus comprising:

an irradiator including a light source which emits light and causes the light to fall on an external measurement mark via a polarizer from an arbitrary direction that would provide a measurement target dimension of a pattern to be measured which is formed on a sample, the measurement mark being formed on the sample in such a manner that measurement patterns in the same shape as at least part of the pattern to be measured are arranged in a matrix constituted of measurement pattern columns repetitively disposed with a predetermined space in the measurement direction, each of the measurement pattern column being composed of the measurement pattern disposed on a predetermined period in a direction perpendicular to the measurement direction;

a detector which detects reflected diffracted light from the measurement mark to measure intensity thereof;

a calculator which receives a plurality of candidate values for the measurement target dimension to calculate a theoretical value of intensity of the reflected diffracted light from the measurement mark, and outputs, as a measurement value of the measurement target dimension, the candidate value which provides a theoretical value most approximate to the measured intensity of the reflected diffracted light; and a wavelength controller which adjusts the wavelength of the incident light in association with said period so that the measurement mark generates the reflected diffracted light which is substantially the same as reflected diffracted light which would be generated when the pattern columns are assumed to be continuous line patterns.

According to a fourth aspect of the invention, there is provided a measurement mark which is formed on a sample so as to include measurement patterns having the same shape as at least part of a pattern to be measured formed on the sample, which generates reflected diffracted light generated by incident light and which is used for dimensional measurement of the pattern to be measured using the reflected diffracted light, wherein the measurement patterns are arranged on a predetermined period in a direction perpendicular to an arbitrary measurement direction that would provide a measurement target dimension to form a measurement pattern column, and said measurement pattern column is repetitively disposed with a predetermined space in the measurement direction, and a value of said period is adjusted in association with the wavelength of the incident light so that the measurement mark generates reflected diffracted light which is substantially the same as reflected diffracted light which would be generated when the pattern column is assumed to be a continuous line pattern.

DETAILED DESCRIPTION OF THE EMBODIMENTS

Several embodiments of the present invention will hereinafter be described in reference to the drawings.

(1) First Embodiment

Figure 1A:
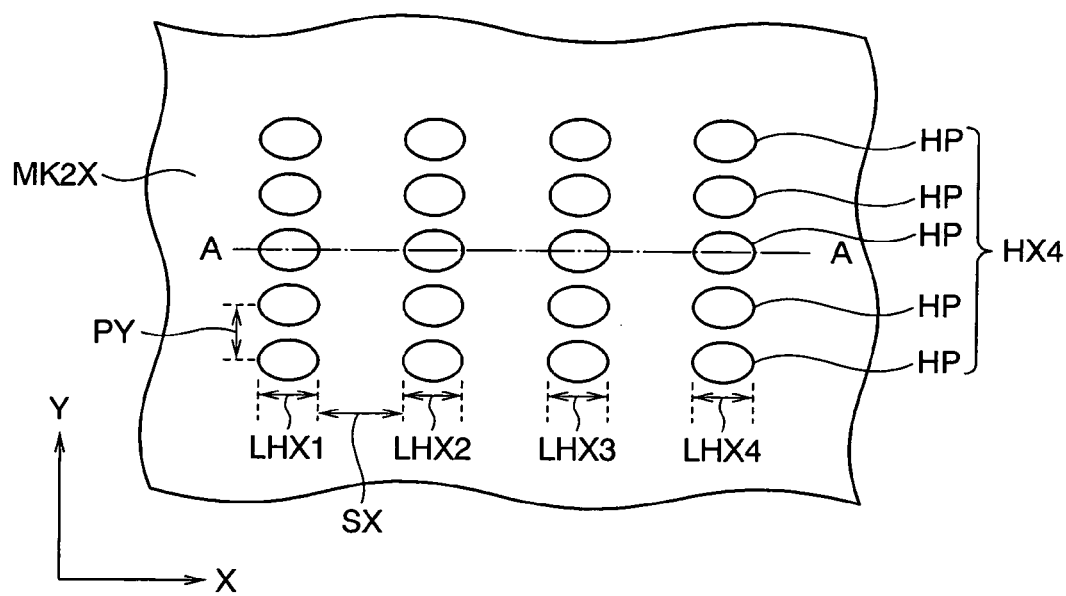
FIG. 1A is a plan view of a portion of a measurement mark according to a first embodiment of the present invention.
Figure 1B:
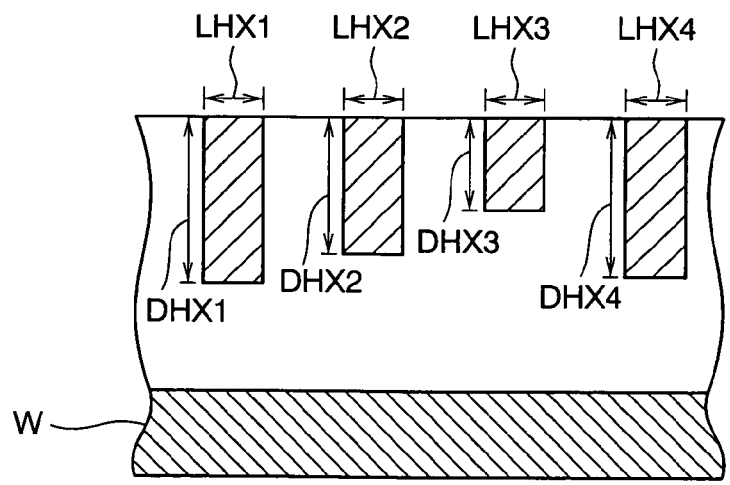
FIG. 1B is a sectional view along the A-A line of FIG. 1A.
Figure 2:
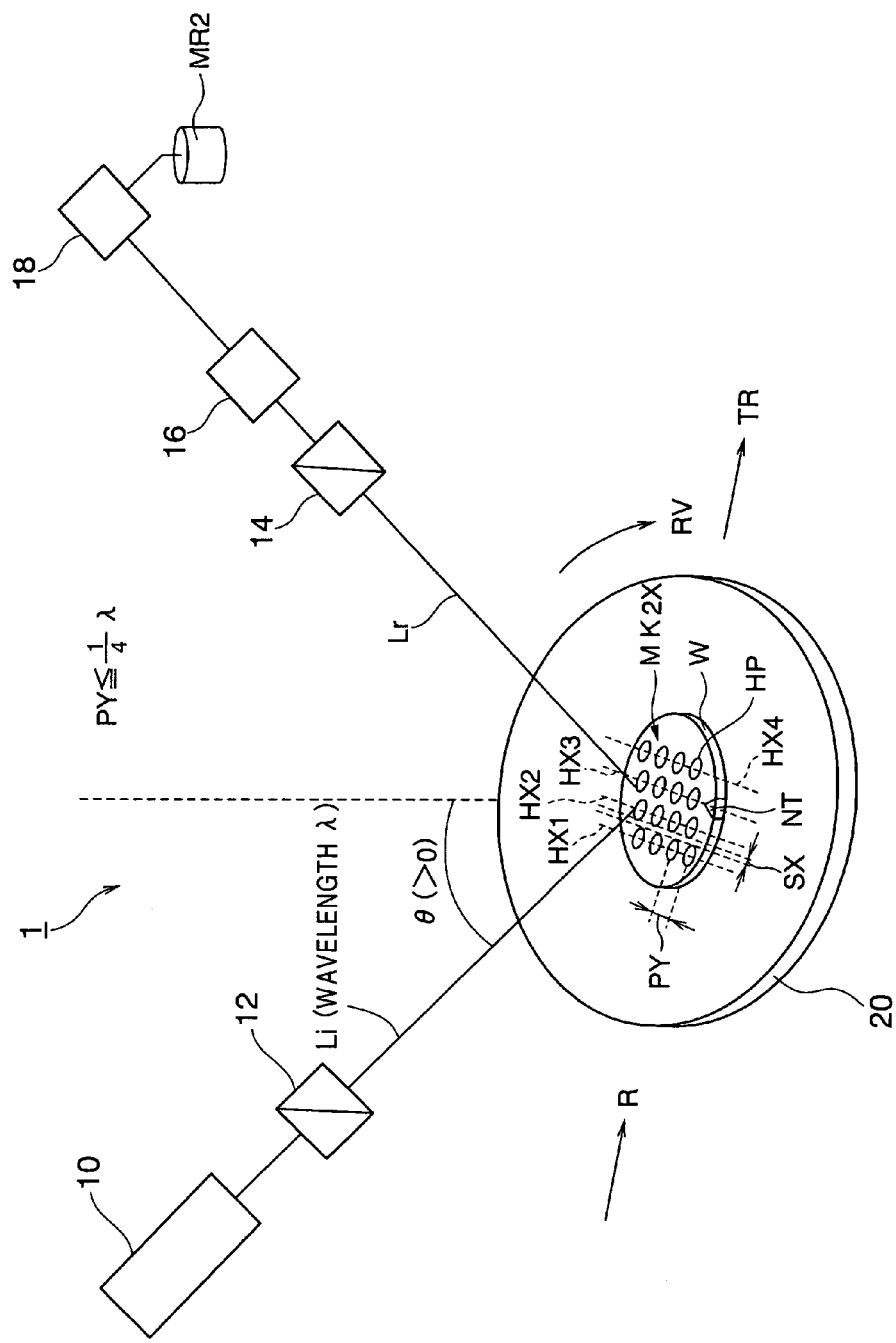
FIG. 2 is a block diagram showing a schematic configuration of a dimension measurement apparatus according to the first embodiment of the present invention.

FIG. 1A is a plan view of a portion of a measurement mark according to the present embodiment, and FIG. 1B is a sectional view along the A-A line of FIG. 1A. FIG. 2 is a block diagram showing a schematic configuration of a dimension measurement apparatus according to the present embodiment.

A measurement mark MK2X shown in FIGS. 1A and 1B is made through formation of a thin film on a semiconductor wafer W with a film material and arrangement of hole patterns HP in a matrix form thereon. The hole patterns HP are first arranged in line as a hole pattern column HX1 on a period PY in a Y direction, and the hole pattern column HX1 is disposed repetitively with a space SX in an X direction, thereby forming a matrix composed of four hole pattern columns HX1 to HX4. Widths of these hole patterns HP in the X direction are LHX1, LHX2, LHX3, LHX4, . . . , respectively, and depths in the X direction are DHX1, DHX2, DHX3, DHX4, . . . , respectively.

The space SX between the hole patterns in the X direction is set to correspond to a space between device patterns which are formed, for example, simultaneously with the hole patterns HP and which are originally targeted for evaluation. Further, the period PY in the Y direction characterizes the present embodiment and is set to be equal to or less than a quarter of a wavelength $\lambda$ of an incident light Li generated by a dimension measurement apparatus 1 shown in FIG. 2.

The dimension measurement apparatus 1 shown in FIG. 2 comprises a light source 10, a polarizer 12, a stage 20, an analyzer 14, an array of detectors 16 including a spectroscope, a computer 18 and a memory MR2. The light source 10 emits white light whose wavelength $\lambda$ is in a range of about 250 to about 800 nm, that is, in the ordinary range from an ultraviolet light to visible light. The stage 20 is driven by an unshown drive device to move the wafer W through revolving movement (RV) and translational movement (TR). The memory MR2 stores measurement profile charts constructed by the computer 18, and also stores a plurality of values which would be candidates for an average value LHXave of widths LHX1, LHX2, LHX3, LHX4, . . . of the hole patterns HP in the X direction and a plurality of values which would be candidates for an average value DHXave of the depths DHX1, DHX2, DHX3, DHX4, . . . of the hole patterns HP in the X direction.

A dimension measurement method using the measurement mark MK2X shown in FIGS. 1A and 1B and the dimension measurement apparatus 1 shown in FIG. 2 will next be described.

First, the wafer W is moved by the revolving movement (RV) and the translational movement (TR) using the stage 20 such that the white light falls on the measurement mark MK2X. In the example shown in FIG. 2, the wafer W is moved so that its notch NT is directed downward of the drawing.

Next, the white light of the wavelength $\lambda$ is emitted by the light source 10, and turned into incident light Li via the polarizer 12, and then caused to obliquely fall on the measurement mark MK2X at an incidence angle $\theta$.

Here, as described above, since the period PY between the hole patterns HP in each hole pattern column HX is set to be equal to or less than a quarter of the wavelength $\lambda$ of the incident light Li, periodic characteristics of the hole patterns HP in the Y direction hardly affect reflected diffracted light Lr. Specifically, in the measurement mark MK2X of the present embodiment, the hole pattern column HX constituted of the hole patterns disposed in the Y direction are not optically separated from each other, the hole pattern column HX in the Y direction optically functions substantially in the same manner as a continuous line pattern. Therefore, the measurement mark MK2X generates the reflected diffracted light Lr which is substantially the same as reflected diffracted light of the continuous line pattern having one-dimensional periodic characteristics in the X direction, that is, reflected diffracted light of the line patterns with widths of LHX1, LHX2, LHX3, LHX4, . . . and with the depths of DHX1, DHX2, DHX3, DHX4, . . . , respectively.

Figure 3:
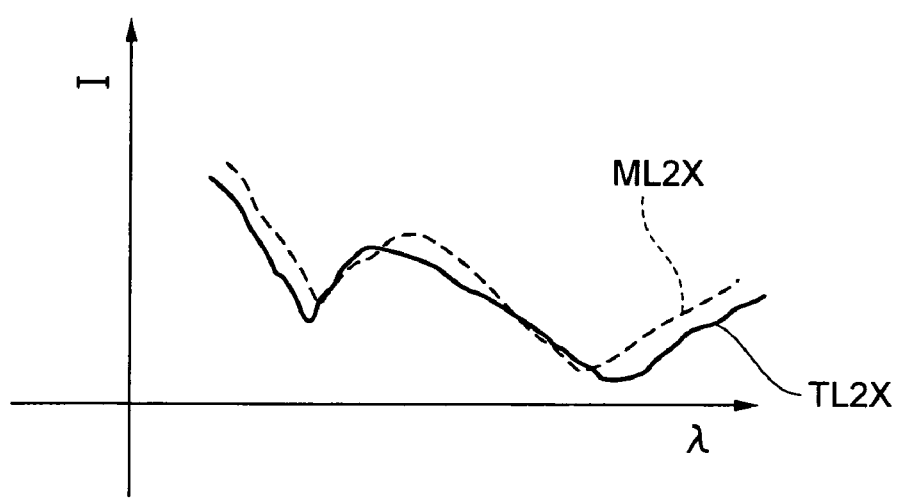
FIG. 3 is a graph showing one example of a measurement profile and a theoretical profile obtained by a dimension measurement method according to the first embodiment of the present invention.

This reflected diffracted light Lr is detected by the detectors 16 via the analyzer 14, and a detection signal thereof is fed to the computer 18. The computer 18 processes the detection signal and plots a measurement profile ML2X in a graph whose horizontal axis indicates a wavelength $\lambda$ and whose vertical axis indicates reflected light intensity I as shown by a broken line in FIG. 3, which is stored by the memory MR100. The computer 18 also derives, from the memory MR2, a plurality of candidate values for the average value LHXave of the widths LHX1, LHX2, LHX3, LHX4, . . . of the hole patterns HP in the X direction and a plurality of candidate values for the average value DHXave of the depths DHX1, DHX2, DHX3, DHX4, . . . of the hole patterns HP in the X direction, in order to substitute these values for a theoretical model such as RCWA. The computer 18 then plots theoretical profiles over the measurement profile ML2X in the graph whose horizontal axis indicates the wavelength $\lambda$ and whose vertical axis indicates reflected light intensity I, and identifies a theoretical profile TL2X which is the most approximate to the measurement profile ML2X among the plotted theoretical profiles as indicated by a full line in FIG. 3, and then outputs, as measurement values, the candidate values for the average values LHXave, DHXave of the widths and depths that have been input when the identified theoretical profile is calculated.

In this way, according to the present embodiment, when shape parameters of the widths and depths of the hole patterns HP in the X direction are measured, the measurement mark MK2X is used which is formed by arranging hole pattern columns HX repetitively with the space SX in the X direction, and in which each of the hole pattern columns HP is arranged on the period PY in the Y direction, and further the period PY is set to a value equal to or less than a quarter of the wavelength $\lambda$ of the incident light, whereby the hole patterns HP in the matrix form optically function in the same manner as one-dimensional line-and-space patterns arranged in the X direction. This makes it possible to simply and rapidly calculate the average value of the widths in the X direction and the average value of the depths in the X direction by use of the conventional theoretical model such as the RCWA method, and as a result, the dimensions of the patterns which are originally targeted for evaluation can be measured highly accurately and rapidly.

The measurement method described above is concerned with the case where the widths and depths of the hole patterns HP constituting the measurement mark are measured in the X direction, but it is also possible to perform measurement in accordance with this method when the widths and depths are desired to be measured in the Y direction.

Figure 4A:
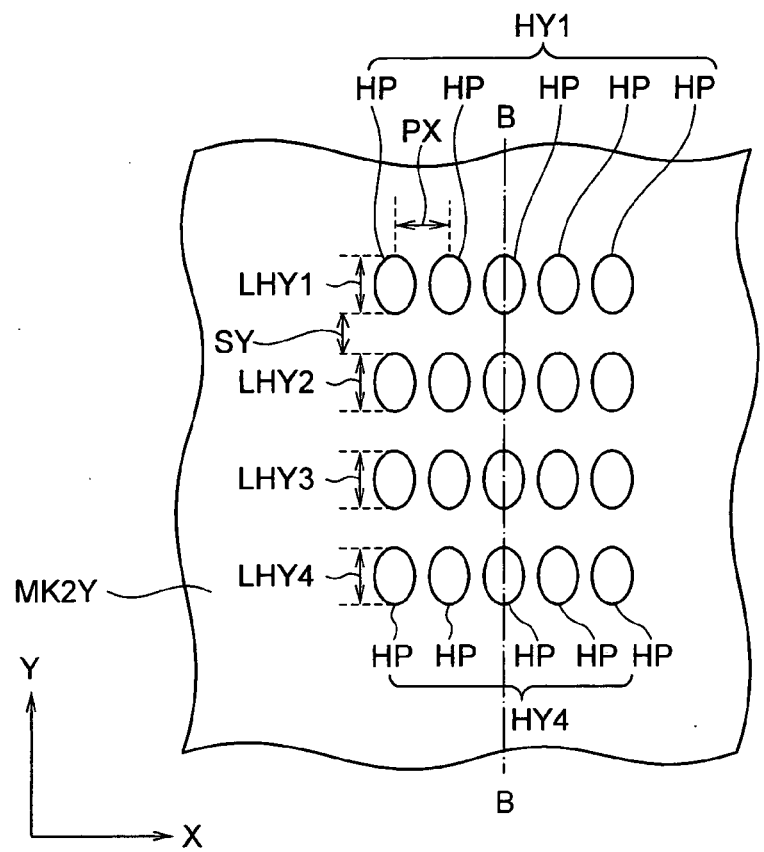
FIG. 4A is a plan view of another portion of the measurement mark according to the first embodiment of the present invention.
Figure 4B:
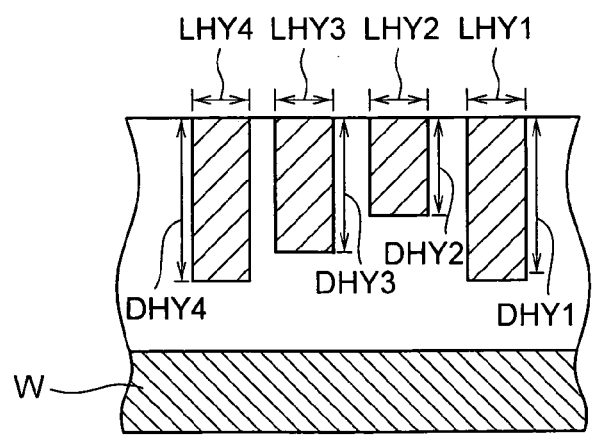
FIG. 4B is a sectional view along the B-B line of FIG. 4A.

Specifically, on the wafer W to be measured, a measurement mark MK2Y is preformed in which a hole pattern column HY1 composed of hole patterns HP2 arranged on a period PX in the X direction therebetween is repetitively arranged with a space SY in the Y direction each other in such a manner as HY2, HY3, HY4, . . . , as shown in FIGS. 4A and 4B. Here, the widths in the Y direction of the hole patterns to be measured are LHY1, LHY2, LHY3, LHY4, . . . as shown in FIG. 4A, and the depths in the Y direction are DHY1, DHY2, DHY3, DHY4, . . . as shown in FIG. 4B. Further, similarly to the measurement mark MK2X described above, the space SY in the Y direction of the hole patterns HP in the measurement mark MK2Y is a distance corresponding to the space between the device patterns which are originally targeted for evaluation, and the period PX in the X direction of the hole patterns HP in the measurement mark MK2Y is set to be equal to or less than a quarter of the wavelength $\lambda$ of the incident light Li.

Figure 5:
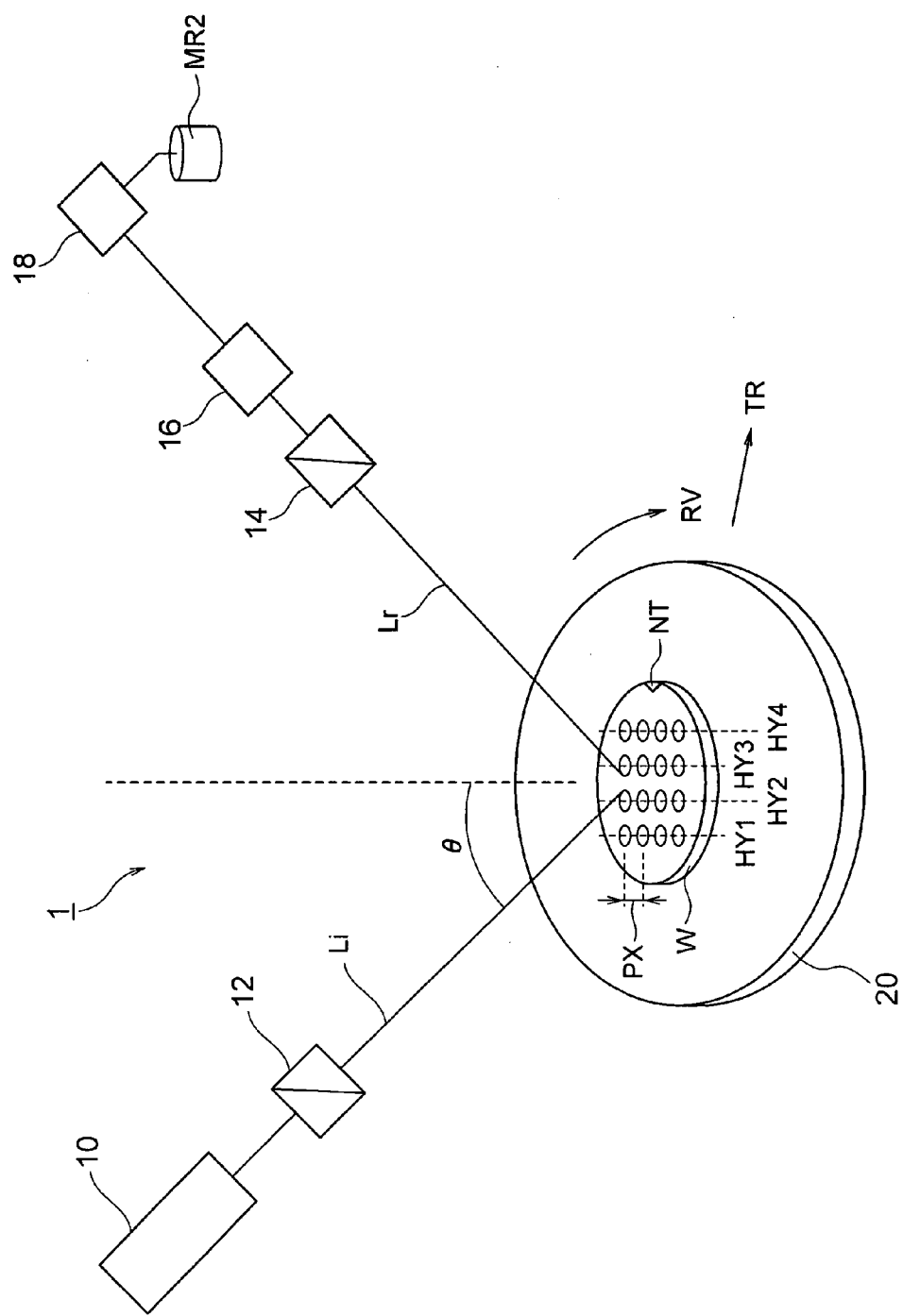
FIG. 5 is a block diagram showing a way of adjusting a positional relation between the measurement mark shown in FIGS. 4A and 4B and incidence direction of an incident light.

In measurement, several candidate values for an average value LHYave of the widths LHY1, LHY2, LHY3, LHY4, . . . of the hole pattern columns HY in the Y direction and several candidate values for an average value DHYave of the depths DHY1, DHY2, DHY3, DHY4, . . . of the hole pattern columns HY in the Y direction are first pre-stored in the memory MR2. Next, the relative position of the wafer W and an optical system of the measurement apparatus 1 is adjusted so that the hole pattern columns HY1 to HY4 will have predetermined angles and positional relations with respect to an incidence direction of the incident light Li. In the example shown in FIG. 5, the wafer W is moved by the revolving movement (RV) and the translational movement (TR) of the stage 20 so that the notch NT of the wafer W is directed rightward of the drawing, thereby adjusting the relative position. Thus, the white light emitted from the light source 10 falls on the measurement mark MK2Y at the incidence angle $\theta$ from a direction that interconnects the hole patterns HP in each of the hole pattern columns HY, that is, from a direction perpendicular to a direction that provides the period PX.

Figure 6:
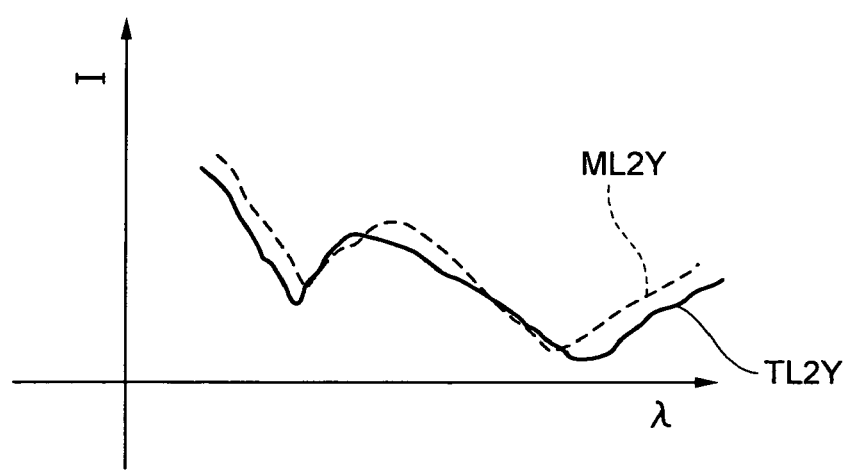
FIG. 6 is a graph showing one example of the measurement profile and the theoretical profile obtained by the measurement mark shown in FIGS. 4A and 4B and the dimension measurement apparatus shown in FIG. 5.

Subsequently, similarly to the measurement for the measurement mark MK2X described above, the reflected diffracted light intensity of the reflected light Lr from the measurement mark MK2Y is measured to obtain its measurement profile ML2Y. In the meantime, several candidates for the theoretical profiles are calculated using the conventional theoretical model such as the RCWA method from the several candidate values for the average value LHYave of the widths of the hole pattern columns HY in the Y direction and several candidate values for the average value DHYave of the depths of the hole pattern columns HY in the Y direction. Then, for example, as shown in FIG. 6, a theoretical profile TL2Y which is the most approximate to the measurement profile ML2Y is identified among the candidate theoretical profiles, and the candidate values for the average values LHYave, DHYave that provide the theoretical profile TL2Y are output as measurement values.

In this way, according to the present embodiment, when the shape parameters of the widths and depths of the hole patterns HP in the Y direction are measured, the hole patterns HP are arranged on the period PX so as to form a column in the X direction, and the hole pattern column HY is arranging repetitively with the space SY in the Y direction to form the measurement mark MK2Y to be used for the measurement, and further the period PX is set to be equal to or less than a quarter of the wavelength $\lambda$ of the incident light, whereby the hole patterns in the matrix form optically functions in the same manner as one-dimensional line-and-space patterns each extending in the Y direction. This makes it possible to simply and rapidly calculate the average value of the widths in the Y direction and the average value of the depths in the Y direction by use of the conventional theoretical model such as the RCWA method, and as a result, the dimensions of the patterns which are originally targeted for evaluation can be measured highly accurately and rapidly.

(2) Second Embodiment

Next, a second embodiment of the present invention will be described referring to FIG. 7 and FIG. 8.

Figure 7:
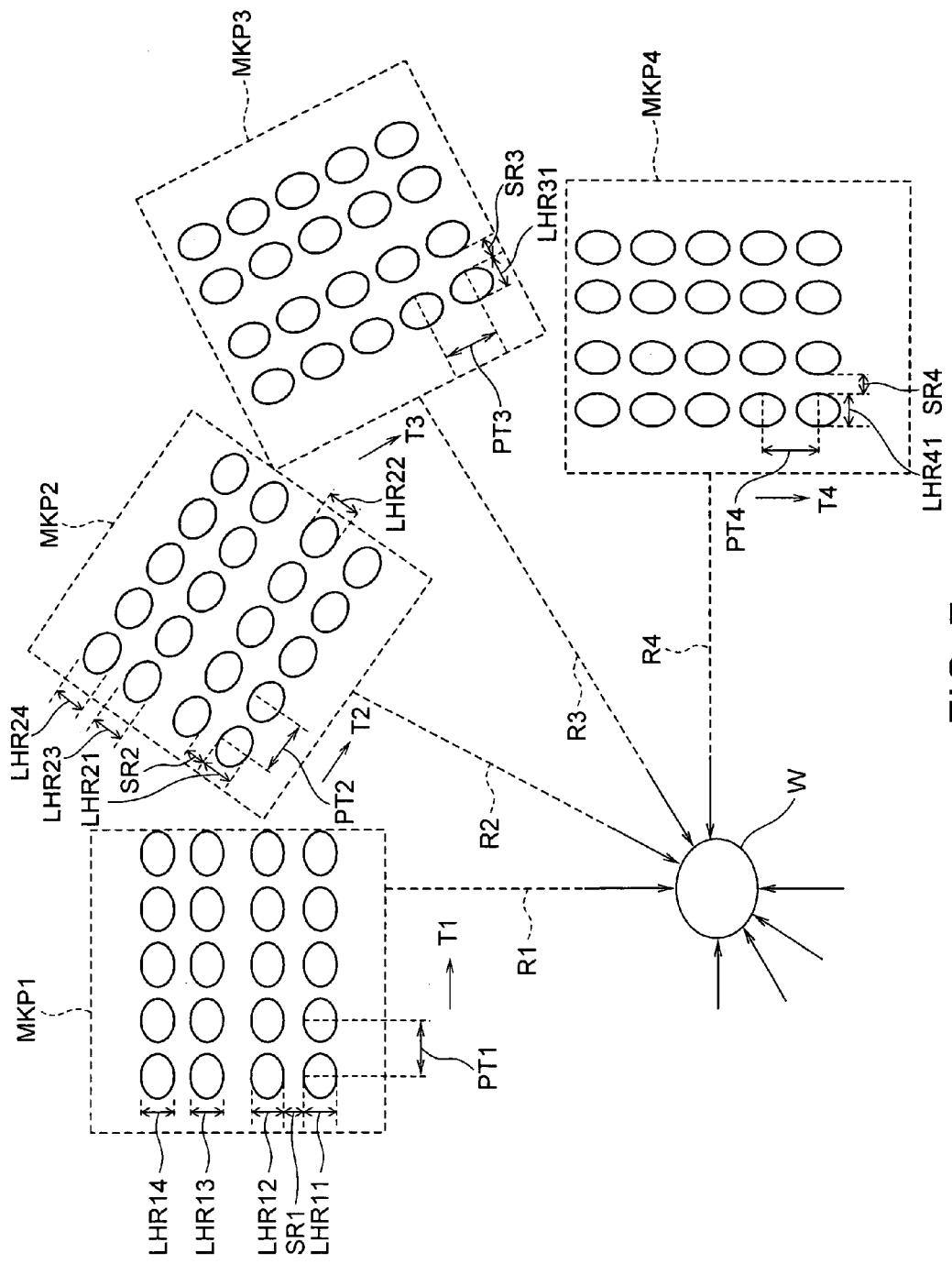
FIG. 7 is an explanatory diagram of schematic configurations of measurement marks according to a second embodiment of the present invention.
Figure 8:
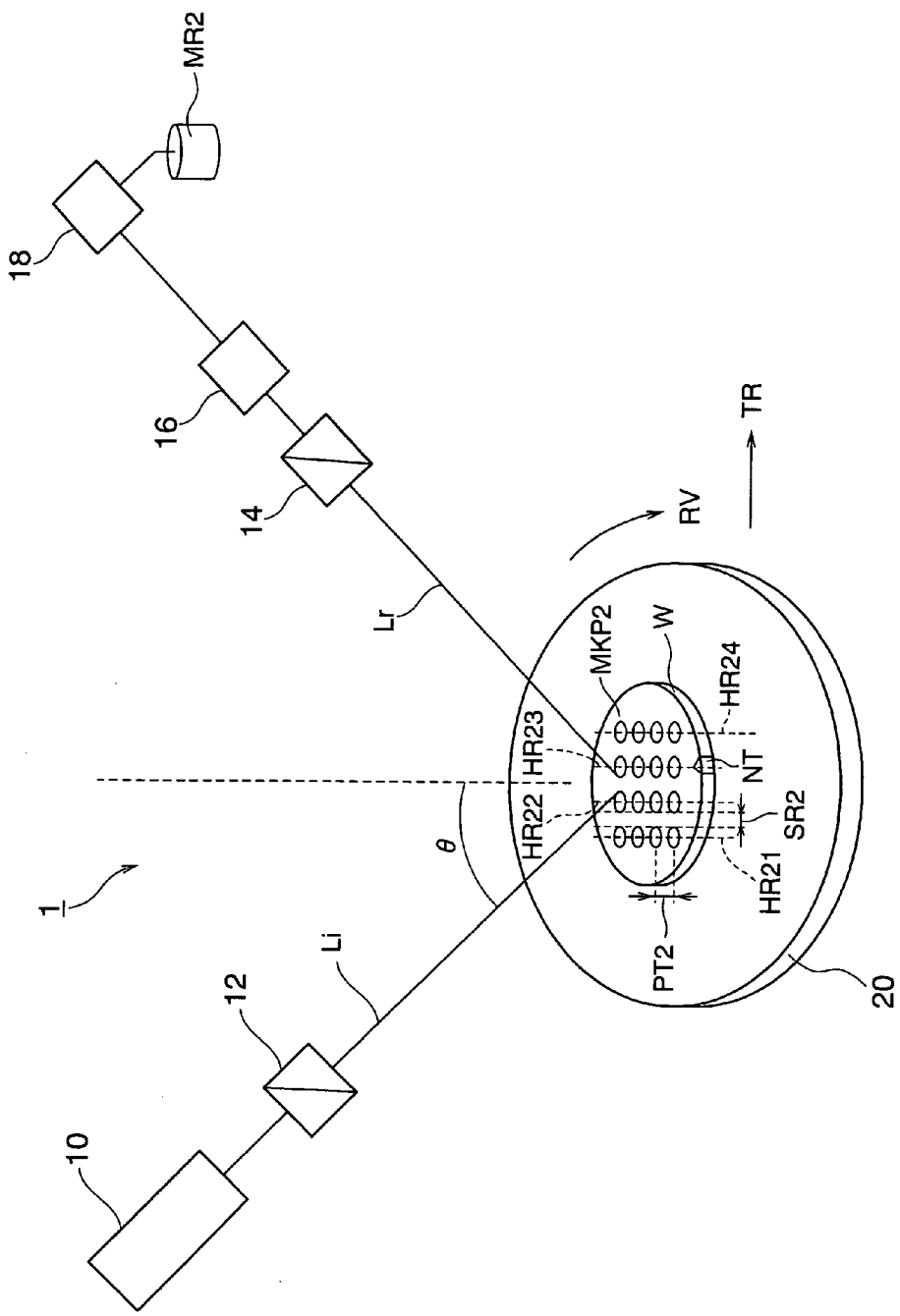
FIG. 8 is an explanatory diagram of a dimension measurement method using the measurement marks shown in FIG. 7.

FIG. 7 is an explanatory diagram of schematic configurations of measurement marks according to the present embodiment, and FIG. 8 is an explanatory diagram of the dimension measurement method using the measurement marks shown in FIG. 7.

First, in the present embodiment, measurement marks MKP1, MKP2, ..., MKPn are provided in peripheral areas of the semiconductor wafer W in accordance with arbitrary measurement directions such as R1, R2, ..., Rn, as shown in FIG. 7. In the example shown in FIG. 7, the measurement directions R1, R2, ..., Rn correspond to diametrical directions of the wafer W. In the measurement marks MKP1, MKP2, ..., MKPn, the hole pattern columns are constituted by the hole patterns HP arranged on periods PT1, PT2, ..., PTn in directions T1, T2, ..., Tn each perpendicular to the measurement directions R1, R2, ..., Rn, and these hole pattern columns are arranged repetitively with spaces SR1, SR2, ..., SRn in the directions R1, R2, ..., Rn, respectively, thereby constituting the measurement marks MKP1, MKP2, ..., MKPn. Similarly to the first embodiment described above, the pattern periods. PT1, PT2, ..., PTn in the hole pattern columns of the measurement marks are set to be equal to or less than a quarter of the wavelength $\lambda$ of the incident light, and each of the spaces SR1, SR2, ..., SRn between hole pattern columns in each of the measurement marks is set to correspond to the space between device patterns which are originally targeted for evaluation. Therefore, from an optical point of view, the hole pattern columns can be regarded as line-and-space line patterns in any of the measurement marks.

The dimension measurement method using the measurement marks MKP1, MKP2, ..., MKPn shown in FIG. 7 is as follows.

First, candidate values for the shape parameters are pre-stored in the memory MR2 of the dimension measurement apparatus 1 (see FIG. 8) for each measurement mark. For example, in the case of the measurement mark MKP2, several candidate values are stored for average values LHR2ave and DHR2ave for widths LHR21 to LHR24 and depths DHR21 to DHR24 (not shown), respectively, of the hole patterns HP in the measurement direction R2.

In measurement, if the measurement mark MKP2 is taken here as an example, the relative position of the wafer W and the optical system of the measurement apparatus 1 is adjusted so that hole pattern columns HR21 to HR24 (in the T2 direction) will have predetermined angles and positional relations with respect to the incidence direction of the incident light Li. In the example shown in FIG. 8, the wafer W is moved by the revolving movement (RV) and the translational movement (TR) of the stage 20 so that the notch NT of the wafer W is directed to the lower right of the drawing, thereby adjusting the above relation. Thus, the white light emitted from the light source 10 falls on the measurement mark MKP2 at the incidence angle θ, for example, from a direction that interconnects the hole patterns HP in the hole pattern column HR21, that is, from the direction perpendicular to the direction that provides the period PT2.

Subsequently, similarly to the measurement for the measurement marks MK2X, MK2Y described above, reflected diffracted light intensity of the reflected light Lr from the measurement mark MKP2 is measured to obtain its measurement profile. In the meantime, several candidates for the theoretical profiles are calculated using the conventional theoretical model such as the RCWA method from the several candidate values for the average value LHR2ave of the widths of the hole pattern columns HR21 to HR24 in the R2 direction and several candidate values for the average value DHR2ave of the depths of the hole pattern columns HR21 to HR24 in the R2 direction. Then, the theoretical profile which is the most approximate to the measurement profile is identified among the calculated candidate theoretical profiles, and the candidate values for the average values LHR2ave, DHR2ave that provide the identified theoretical profile are output as measurement values.

The other measurement marks can be measured in accordance with the measurement method applied to the measurement mark MKP2 described above.

In this way, according to the present embodiment, since the measurement marks MKP1, MKP2, ..., MKPn formed in the directions corresponding to the arbitrary measurement directions such as R1, R2, ..., Rn are provided on the semiconductor wafer W, respectively, the measurement mark corresponding to the direction in which the device patterns to be evaluated are disposed can be selected to measure its shape parameters rapidly and highly accurately.

(3) Third Embodiment

Next, a third embodiment of the present invention will be described referring to FIG. 9 to FIG. 11. The cylindrical hole patterns HP are measured in the embodiments described above, but the present invention is not limited to these shapes and can also be applied to patterns having arbitrary shapes.

Figure 9:
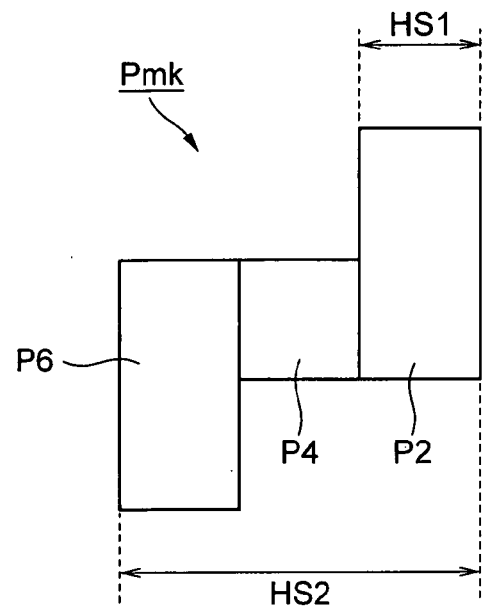
FIG. 9 is a plan view of one example of a device pattern to be evaluated.

FIG. 9 is a plan view of one example of a device pattern to be evaluated. A pattern Pmk shown in FIG. 9 has three patterns P2, P4 and P6 that are sequentially arranged to be combined. In the case of the pattern to be evaluated having such a shape, when a width HS1 in the lateral direction of the pattern P2 is desired to be measured, a measurement mark may be prepared in which the pattern P2 having the width HS1 is arranged on a period Phs1 to form a pattern column and the pattern column thus produced is arranged repetitively in the direction of the width HS1, wherein the period Phs1 is equal to or less than a quarter of the wavelength $\lambda$ of the incident light in a direction perpendicular to the direction that provides the width HS1.

Figure 11:
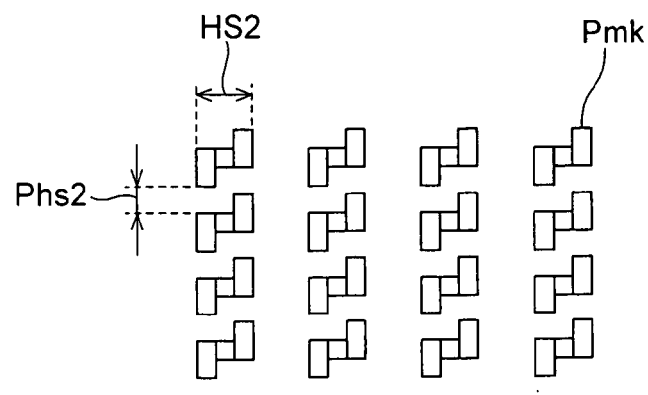
FIG. 11 is a plan view of another example of the measurement mark constituted of patterns having an arbitrary shape.

Furthermore, in the pattern Pmk shown in FIG. 9, when a maximum width HS2 in a direction parallel with the width HS1 is desired to be measured, the patterns Pmk are arranged on a period Phs2, which is equal to or less than a quarter of the wavelength $\lambda$ of the incident light, in a direction perpendicular to the direction that provides the width HS2 to form a pattern column, and a measurement mark may be prepared which is constituted by arranging this pattern column repetitively in the direction of the width HS2, as shown in a plan view of FIG. 11.

Figure 10:
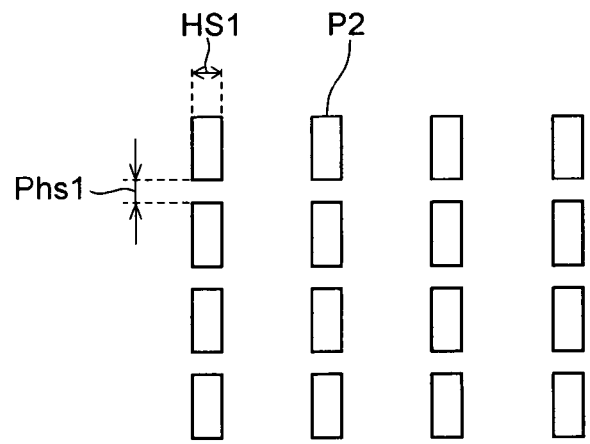
FIG. 10 is a plan view of one example of the measurement mark constituted of patterns having an arbitrary shape.

Since the measurement method used in the first and second embodiments described above can be applied to both of the measurement marks in FIG. 10 and FIG. 11, candidates for the theoretical profile can be easily calculated by the conventional theoretical model. Thus, for patterns having an arbitrary shape, their dimensions can also be measured rapidly and highly accurately.

(4) Fourth Embodiment

In the embodiments described above, the pattern dimensions are measured using the optical system having an ellipsometric arrangement in which the light obliquely falls on the measurement mark. However, the present invention is not limited to these forms and can also be applied when a reflective spectroscopy in which incidence is normal is used wherein the direction of the light is perpendicular to a surface of a specimen. An embodiment of measuring the pattern dimensions using such a spectroscopic reflecting optical system will be described referring to FIG. 12.

Figure 12:
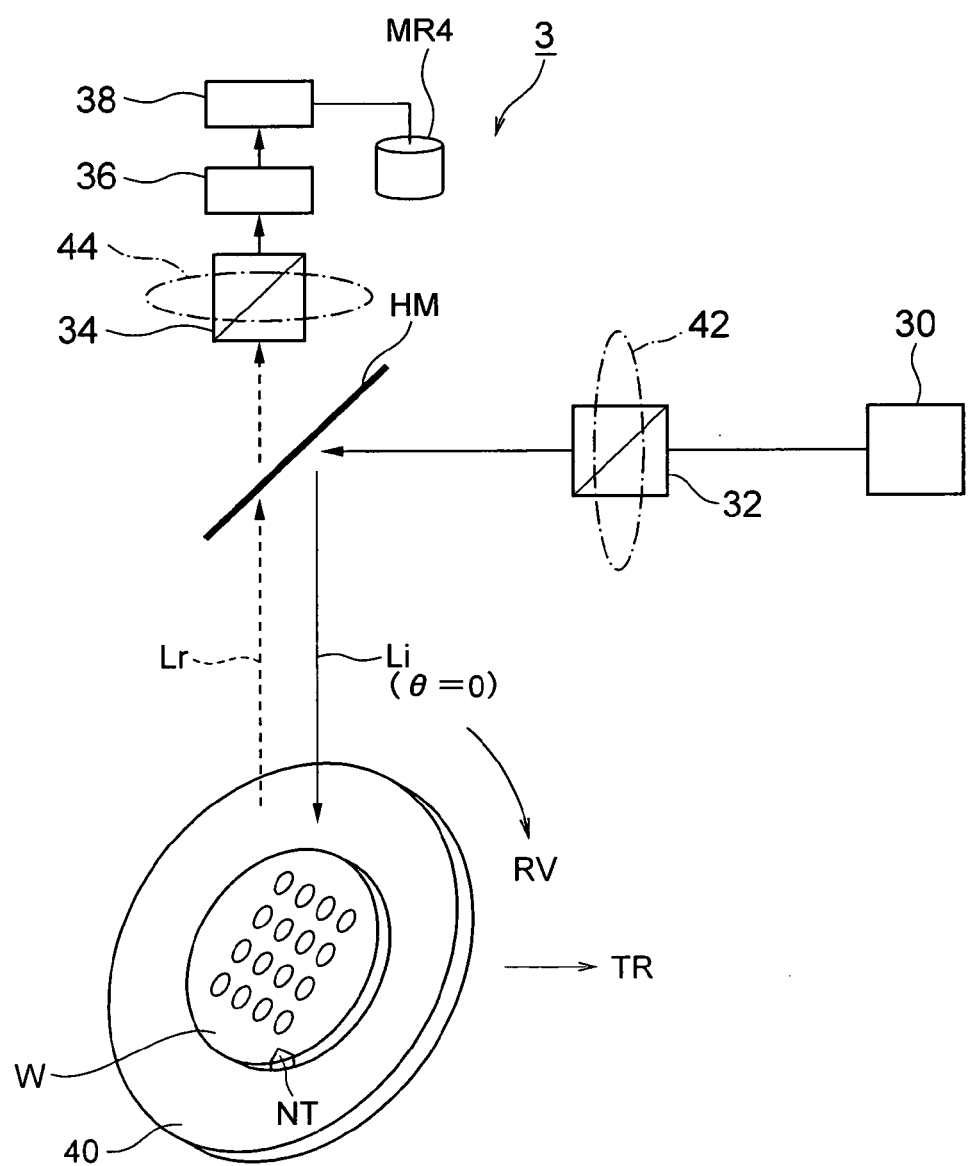
FIG. 12 is a block diagram showing a schematic configuration of the dimension measurement apparatus according to a fourth embodiment of the present invention.
Figure 13A:
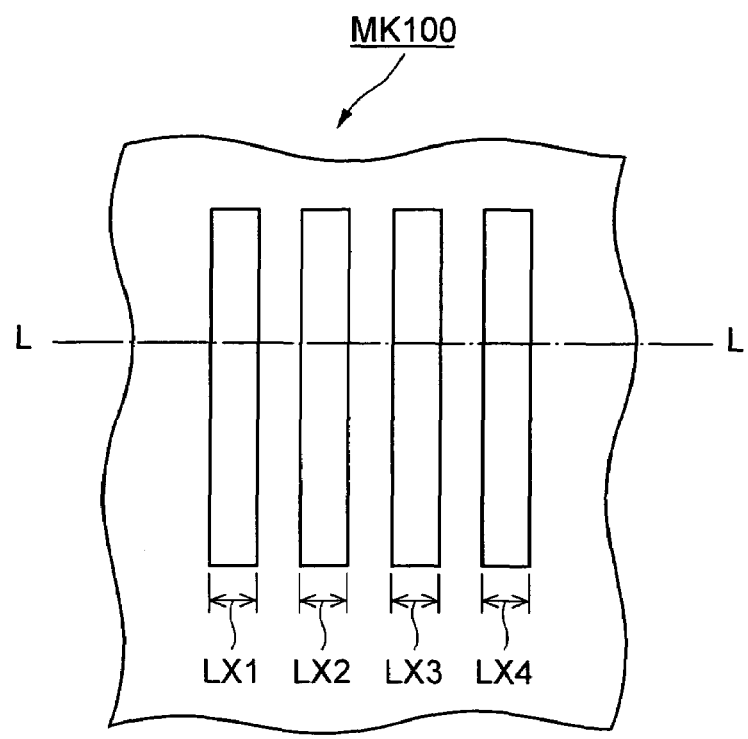
FIGS. 13A and 13B show one example of the measurement mark according to the related conventional art.
Figure 13B:
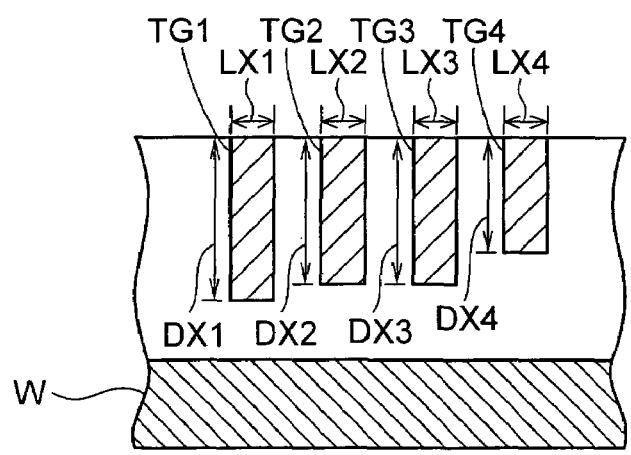
Figure 14:
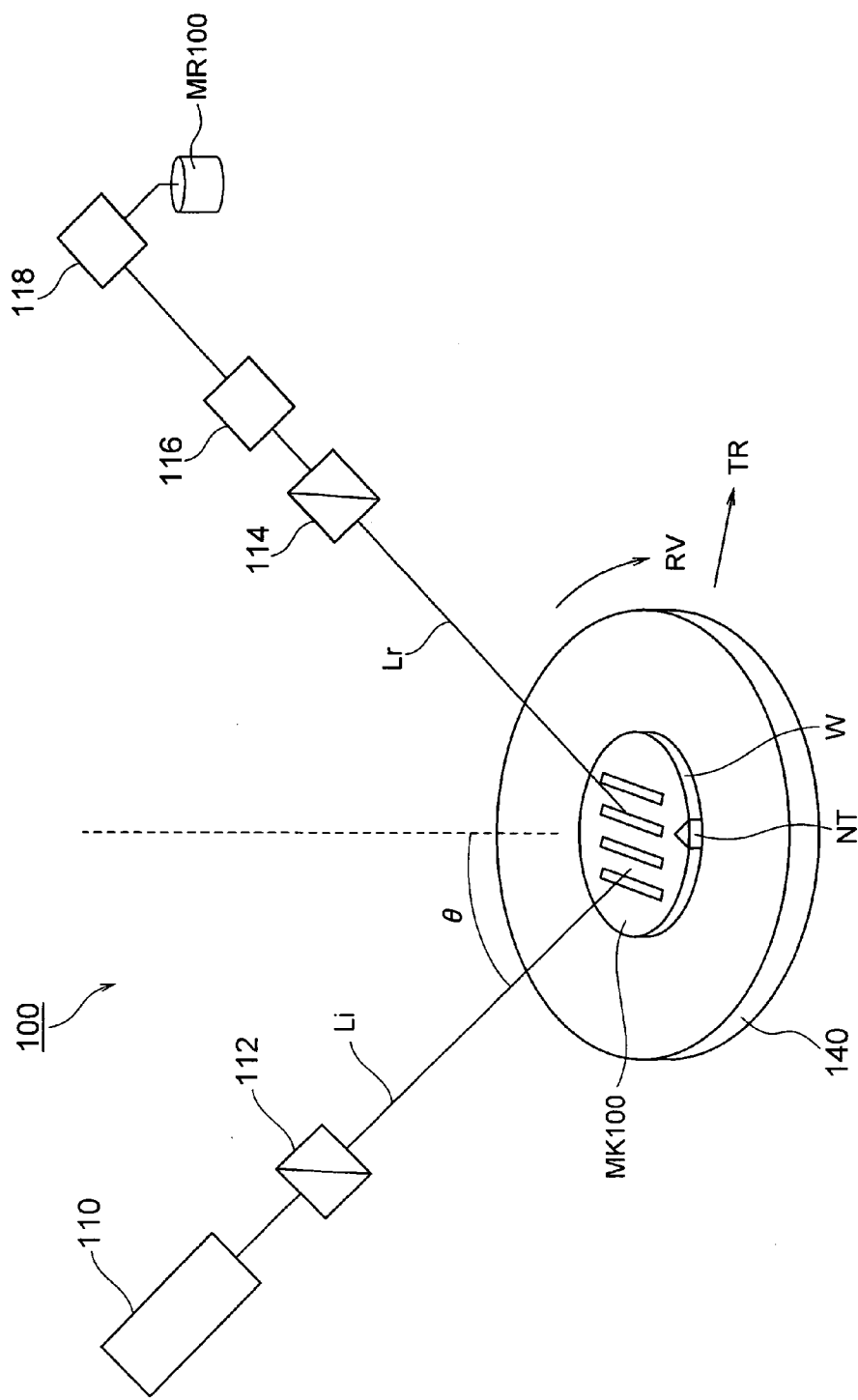
FIG. 14 is a block diagram showing one example of the dimension measurement apparatus according to the related conventional art.
Figure 15:
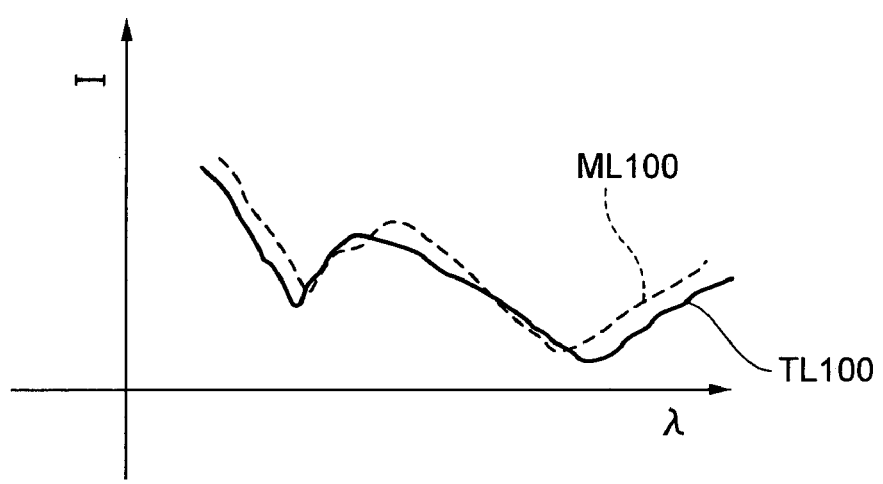
FIG. 15 is a profile chart explaining one example of the dimension measurement method according to the related conventional art.
Figure 16A:
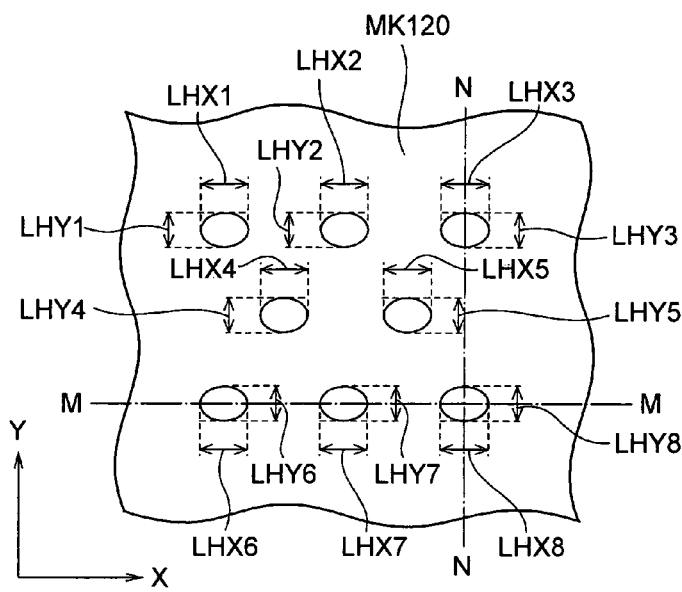
FIG. 16A is a plan view of one example of the measurement mark constituted of cylindrical hole patterns.
Figure 16B:
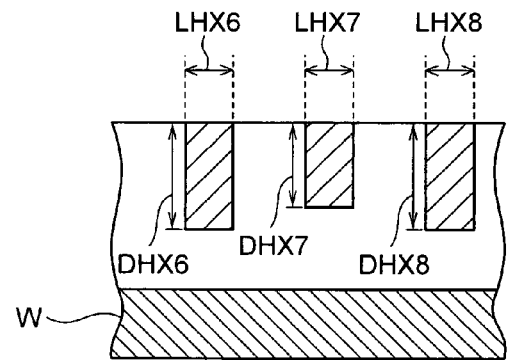
FIG. 16B is a sectional view along the M-M line of FIG. 16A.
Figure 16C:
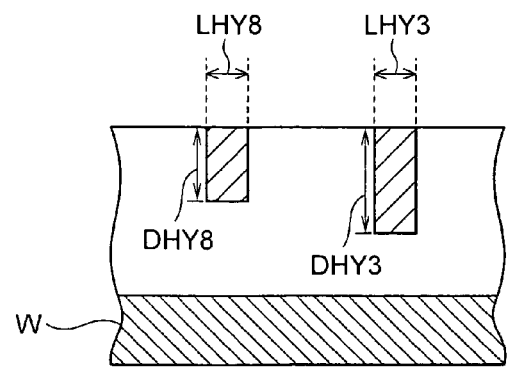
FIG. 16C is a sectional view along the N-N line of FIG. 16A.
Figure 17:
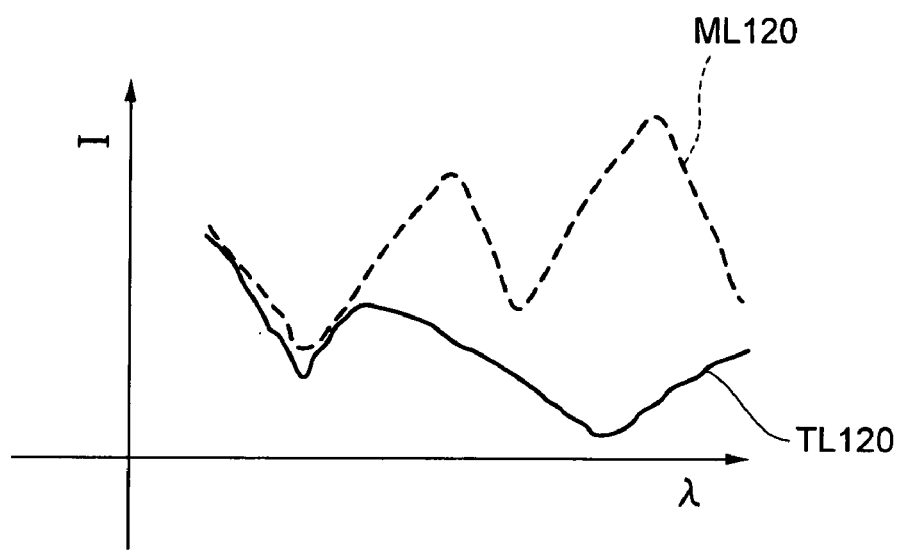
FIG. 17 is a profile chart explaining problems of the dimension measurement method according to the related conventional art.

FIG. 12 is a block diagram of one embodiment of the dimension measurement apparatus comprising the reflective spectroscopy in which incidence is normal. A dimension measurement apparatus 3 shown in FIG. 12 comprises a light source 30, a polarizer 32, a polarizer rotational drive mechanism 42, a half mirror HM, a stage 40 driven by a drive device (not shown), an analyzer 34, an analyzer rotational drive mechanism 44, an array of detectors 36 including a polarizer, a computer 38 and a memory MR4. The light source 30 emits white light having a wavelength λ. The half mirror HM reflects the white light via the polarizer 32 to cause it to fall perpendicularly (θ=0) on the measurement mark. On the other hand, the half mirror HM transmits the reflected diffracted light from the measurement mark therethrough so that the detectors 36 detect it via the analyzer 34. The polarizer rotational drive mechanism 42 rotates the polarizer 32 through revolving movement on an optical axis from the light source 30 to the half mirror HM, thereby adjusting the relative position of an primary optical system and a measurement target so that an electric field parallel with or perpendicular to the pattern columns of the measurement mark is formed on the measurement target. This adjustment is not exclusively performed by the rotation of the polarizer 32, and can also be implemented by causing the analyzer rotational drive mechanism 44 to rotate the analyzer 34 on an optical axis of the reflected diffracted light. Similarly to the memory MR2 described above, the memory MR4 stores the measurement profile charts created by the computer 38, and also stores candidate values for the shape parameters in the desired measurement direction of the patterns constituting the measurement mark.

The dimension measurement method using the dimension measurement apparatus 3 shown in FIG. 12 is substantially the same as those in the embodiments described above, and therefore will not be described.

As long as a measurement mark is used in which the pattern column whose period in the direction perpendicular to the measurement direction is equal to or less than a quarter of the incident light λ is repetitively arranged in the direction of the measurement direction, candidates for the theoretical profile can also be simply and rapidly calculated with the conventional theoretical model by use of the dimension measurement apparatus comprising the reflective spectroscopy in which incidence is normal as shown in FIG. 12. Thereby, the shape parameters of the device pattern to be evaluated can be measured highly accurately and rapidly.

(5) Method of Manufacturing Semiconductor Device

The dimensions of the pattern to be evaluated can be measured highly accurately and rapidly by using the dimension measurement method described above in a manufacturing process of a semiconductor device, so that the semiconductor device can be manufactured with a high yield ratio.

While the embodiments of the present invention have been described above, the present invention is not limited to the above embodiments, and various modifications can be applied within the scope thereof. For example, the wafer W is moved by the revolving movement and the translational movement of the stage to adjust the relative position of the optical system of the measurement apparatus and the measurement mark in the first and second embodiments, but without limiting to this form, at least one of the primary optical system from the light emission to incidence and a secondary optical system from the occurrence of the reflected diffracted light to its detection may be rotated to adjust the relative position as in the fourth embodiment. Further, in the embodiments described above, the relative position is adjusted so that the electric field parallel with or perpendicular to the pattern columns of the measurement mark is formed on the measurement target, but the angle between an electric field plane of the incident light and the pattern column is not limited to the parallel and perpendicular angles, and the present invention is also applicable to dimensional measurement which is applied in spectroscopic ellipsometry. In this case, for example, angles in a predetermined range $\psi a$ to $\psi b$ are set, and the incident light is sequentially applied to the pattern column so that the electric field plane forms the angles $\psi a$ to $\psi b$ with the pattern column, and then reflected diffracted light intensities Ia to Ib are measured, such that a phase difference $\Delta$ and an amplitude ratio $\phi$ of the reflected diffracted light when the incident light would be applied to the pattern columns in parallel and perpendicularly may be calculated from the obtained reflected diffracted light intensities Ia to Ib. In addition, the above embodiments have been described with the analyzer as a wavelength selector, but this is not a limitation, and a wavelength filter can be used instead of the analyzer, for example.

What is claimed is:

1. A dimension measurement method comprising:
   irradiating a measurement mark with light, the measurement mark being formed on a sample on which a pattern to be measured is formed, the measurement mark comprising measurement patterns of the same shape as at least part of the pattern to be measured, the measurement patterns being arranged in a matrix constituted of measurement pattern columns which are repetitively disposed with a predetermined space in the direction of an arbitrary measurement direction which would provide a measurement target dimension of the pattern to be measured, said measurement pattern column being composed of the measurement patterns disposed with a predetermined period in the direction perpendicular to the measurement direction, and the light being fallen from the measurement direction;
   detecting reflected diffracted light from the measurement mark to measure intensity thereof;
   calculating a theoretical value of the intensity of the reflected diffracted light from a plurality of candidate values for the measurement target dimension; and
   outputting, as a measurement value of the measurement target dimension, the candidate value which provides a theoretical value most approximate to the measured intensity of the reflected diffracted light among the plurality of candidate values,
   wherein a relation between a wavelength of the light incident on the measurement mark and said period is adjusted so that the measurement mark generates the reflected diffracted light which is substantially the same as reflected diffracted light which would be generated when said pattern column is assumed to be a continuous line pattern.

2. The dimension measurement method according to claim 1,
   wherein if the wavelength of the incident light is λ and the period is P, the following equation is formulated:
   $P \leq a\lambda$ (a is a constant number of about a quarter).

3. The dimension measurement method according to claim 1, wherein if the period is P and the wavelength of the incident light is λ, the value of the wavelength λ is selected so that the following equation is formulated:

P ≦ aλ (a is a constant number of about a quarter).

4. The dimension measurement method according to claim 1,
wherein the measurement pattern is a cylindrical hole pattern.

5. The dimension measurement method according to claim 1,
wherein the measurement pattern is a single rectangular hole pattern or a plurality of rectangular hole patterns which are sequentially arranged to be combined.

6. A method of manufacturing a semiconductor device, comprising a dimension measurement method including:
irradiating a measurement mark with light, the measurement mark being formed on a sample on which a pattern to be measured is formed, the measurement mark comprising measurement patterns of the same shape as at least part of the pattern to be measured, the measurement patterns being arranged in a matrix constituted of measurement pattern columns which are repetitively disposed with a predetermined space in the direction of an arbitrary measurement direction which would provide a measurement target dimension of the pattern to be measured, said measurement pattern column being composed of the measurement patterns disposed with a predetermined period in the direction perpendicular to the measurement direction, and the light being fallen from the measurement direction;
detecting reflected diffracted light from the measurement mark to measure intensity thereof;
calculating a theoretical value of the intensity of the reflected diffracted light from a plurality of candidate values for the measurement target dimension; and
outputting, as a measurement value of the measurement target dimension, the candidate value which provides a theoretical value most approximate to the measured intensity of the reflected diffracted light among the plurality of candidate values,
wherein a relation between a wavelength of the light incident on the measurement mark and said period is adjusted so that the measurement mark generates the reflected diffracted light which is substantially the same as reflected diffracted light which would be generated when said pattern column is assumed to be a continuous line pattern.

7. The method of manufacturing a semiconductor device according to claim 6,
wherein if the wavelength of the incident light is λ and the period is P, the following equation is formulated:

P ≦ aλ (a is a constant number of about a quarter).

8. The method of manufacturing a semiconductor device according to claim 6,
wherein if the period is P and the wavelength of the incident light is λ, the value of the wavelength λ is selected so that the following equation is formulated:

P ≦ aλ (a is a constant number of about a quarter).

9. The method of manufacturing a semiconductor device according to claim 6,
wherein the measurement pattern is a cylindrical hole pattern.

10. The method of manufacturing a semiconductor device according to claim 6,
wherein the measurement pattern is a single rectangular hole pattern or a plurality of rectangular hole patterns which are sequentially arranged to be combined.

11. A dimension measurement apparatus comprising:
an irradiator including a light source which emits light and causes the light to fall on an external measurement mark via a polarizer from an arbitrary direction that would provide a measurement target dimension of a pattern to be measured which is formed on a sample, the measurement mark being formed on the sample in such a manner that measurement patterns in the same shape as at least part of the pattern to be measured are arranged in a matrix constituted of measurement pattern columns repetitively disposed with a predetermined space in the measurement direction, each of the measurement pattern column being composed of the measurement pattern disposed on a predetermined period in a direction perpendicular to the measurement direction;
a detector which detects reflected diffracted light from the measurement mark to measure intensity thereof;
a calculator which receives a plurality of candidate values for the measurement target dimension to calculate a theoretical value of intensity of the reflected diffracted light from the measurement mark, and outputs, as a measurement value of the measurement target dimension, the candidate value which provides a theoretical value most approximate to the measured intensity of the reflected diffracted light; and
a wavelength controller which adjusts the wavelength of the incident light in association with said period so that the measurement mark generates the reflected diffracted light which is substantially the same as reflected diffracted light which would be generated when the pattern columns are assumed to be continuous line patterns.

12. The dimension measurement apparatus according to claim 11, further comprising
a position adjuster which adjusts a positional relation between at least one of the polarizer and detectors, and the measurement mark so that an electric field plane of the incident light forms a predetermined angle with the direction of the measurement pattern column, thereby enabling one-dimensional reflected diffracted light to be obtained from the measurement mark.

13. The dimension measurement apparatus according to claim 11, wherein
the light source and the polarizer constitute an optical system having an ellipsometric arrangement.

14. The dimension measurement apparatus according to claim 11, wherein
the light source and the polarizer constitute a reflective spectroscopy in which incidence is normal.

* * * * *